United States Patent [19]

Vaillancourt

[11] Patent Number: 5,234,411
[45] Date of Patent: Aug. 10, 1993

[54] CATHETER ASSEMBLY

[76] Inventor: Vincent L. Vaillancourt, 14 Bunyan Dr., (County of Essex) Livingston, N.J. 07039

[21] Appl. No.: 811,654

[22] Filed: Dec. 23, 1991

[51] Int. Cl.⁵ .................. A61M 5/00; A61M 5/32; A61M 5/178
[52] U.S. Cl. .................. 604/171; 604/163; 604/158
[58] Field of Search .......... 604/158, 163, 164, 171, 604/172, 905

[56] References Cited

U.S. PATENT DOCUMENTS

| | | | |
|---|---|---|---|
| 3,825,001 | 7/1974 | Bennet et al. | 604/171 |
| 4,235,232 | 11/1980 | Spaven et al. | 604/171 |
| 4,326,520 | 4/1982 | Alley | 604/171 |
| 4,634,433 | 1/1987 | Osborne | 104/171 |
| 4,767,409 | 8/1988 | Brooks | 604/171 |
| 5,147,314 | 9/1992 | Vaillancourt | 604/158 |

FOREIGN PATENT DOCUMENTS 2847455  3/1979  Fed. Rep. of Germany ...... 604/171

*Primary Examiner*—Gene Mancene
*Assistant Examiner*—Cindy A. Cherichetti

[57] ABSTRACT

The catheter assembly has a shielded unit in which a distal end of a catheter is sealed within a collapsible sheath in a sterile manner. One end of the sheath is secured to a hub which is slidable on the catheter in seal-fit relation and the other end of the sheath is secured to a connector which contains a hollow needle for passage of the catheter and a sealing membrane to seal off the connector. The catheter assembly also has an introducer which is provided with a sealing membrane which can be pierced by the hollow needle as the connector is coupled with the introducer. A container assembly is also provided which has a pierceable membrane through which the hollow needle of the connector may pass to permit pre-inflation of the balloon for use in conjunction with a flow directed type catheter for viewing the expansion of the balloon-tipped end of the flow directed type catheter within the sealed chamber of the container assembly.

A kit comprising the catheter assembly including an introducer or container assembly or both as is taught herein is also provided.

9 Claims, 2 Drawing Sheets

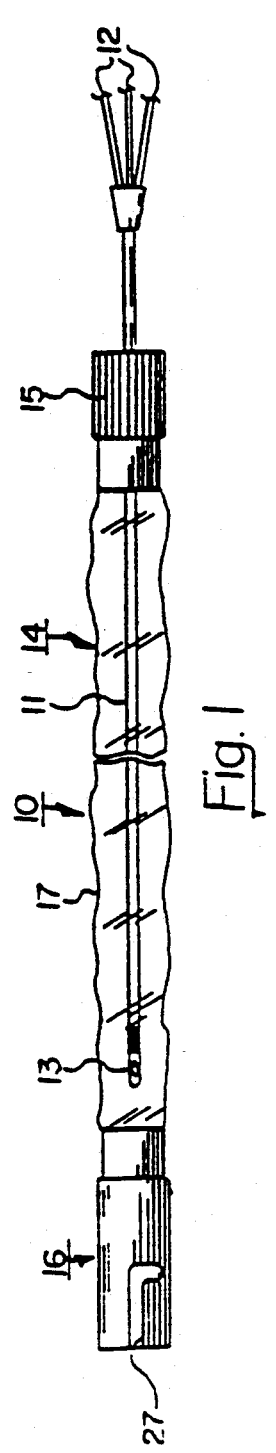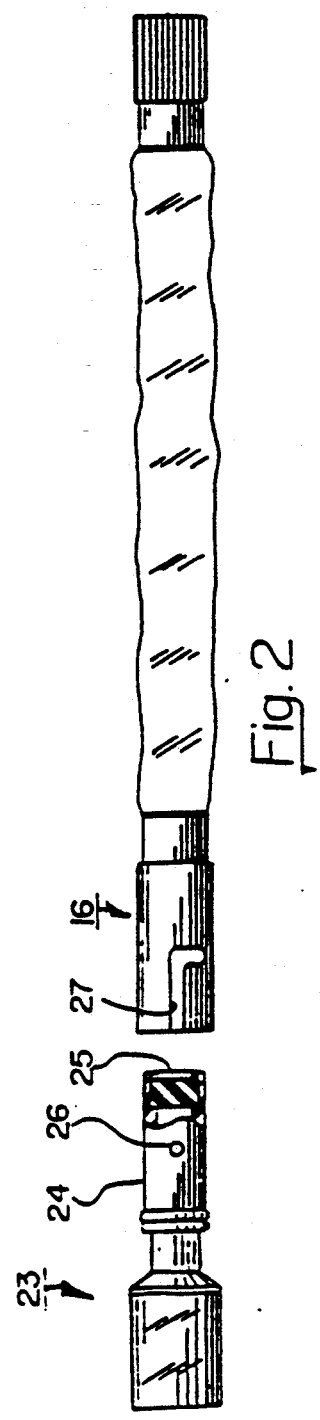

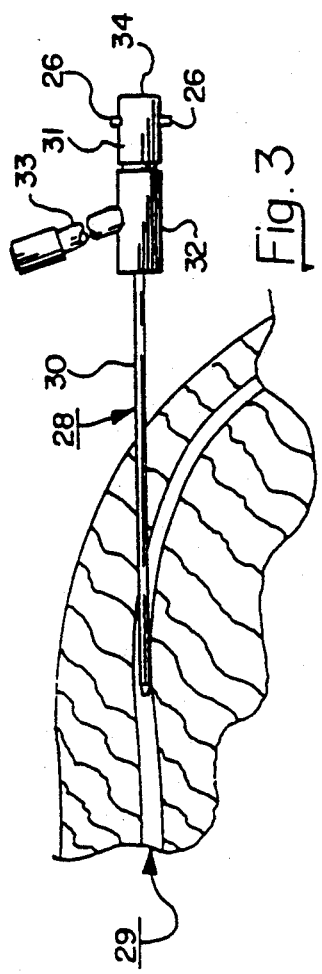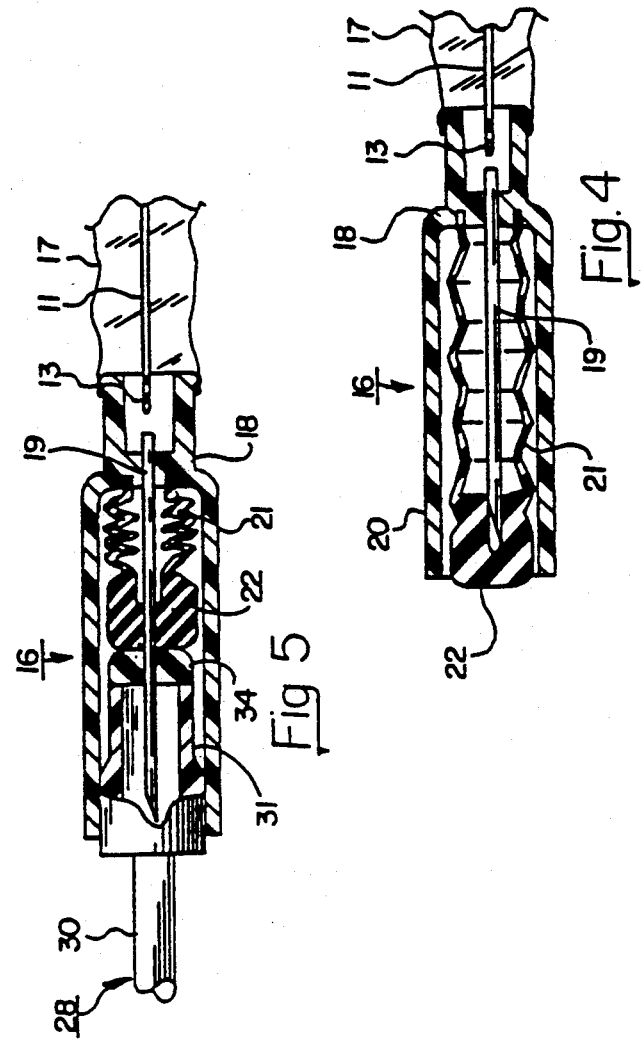

CATHETER ASSEMBLY

This invention relates to a catheter assembly.

Heretofore, various types of catheter assemblies have been known for introduction into the blood vessels of a patient. For example, one known catheter assembly which has been used in the measurement of central venous pressure and pulmonary wedge pressure during and after cardio-pulmonary bypass surgical procedures employs a pulmonary article balloon-tipped catheter, such as described in U.S. Pat. No. 4,327,723 and are generally known to the art as a "flow directed type" catheter. Generally, catheter assemblies of this type employ a catheter with a plurality of lumens, one of which is in communication with the inflatable balloon located immediately adjacent the catheter tip. The other lumen have been connected to individual tubes which serve various purposes, for example for inflating the balloon, dispensing medicine and the like. Other known catheters in widespread use lack a pulmonary balloon as has been heretofore described.

Catheter assemblies of either the flow directed type which comprise a balloon or alternatively catheter assemblies which do not include a balloon are generally supplied to a physician in a sterile condition, frequently in a sealed sterile pouch or other type container, which sterile pouch or container retains its contents in a sterile environment until opened. Further, in order to minimize contamination, the catheter tip may be supplied encased within a tube or be inserted into a tube having a closed container at the distal end. This closed container allows the practitioner to pre-inflate the balloon of a flow-directed type catheter in order to check the balloon for leakage by visual inspection and to flush out the catheter when desired. After the balloon is deflated, the container and tube covering the distal portion of the catheter is usually removed. The catheter is then inserted into an introducer catheter which has been previously placed in a blood vessel and is subsequently moved until being properly located, for example, being advanced to a wedge position. As described in U.S. Pat. No. 4,327,723, a previously positioned catheter sheath which covers a portion of the catheter can then be moved forward to join to the proximal end of the introducer catheter in order to provide a shield for most of the exposed portion of the catheter and to allow repositioning should the catheter become dislodged or moved.

However, in catheter assemblies of the above type, once the tube encasing the catheter, especially the catheter tip is moved, the catheter tip and the catheter is exposed to contamination. Further, should repositioning of the catheter be required and necessitate the partial or total removal of the catheter from a patient into the atmosphere, such exposure may subject the withdrawn portions of the catheter to contamination. Reinsertion of the catheter which has been thus exposed brings with it a concomitantly increased risk of introducing a contaminant into the blood vessel.

Accordingly, it is an object of the invention to protect all parts of a catheter assembly which come in contact with a patient at all times.

It is another object of the invention to be able to reposition an external extended portion of a catheter assembly while maintaining the portion in a sterilized condition.

It is another object of the invention to allow a practitioner to pre-inflate or otherwise check a balloon of a flow directed type catheter for integrity as well as to flush the catheter under sterile conditions without exposing the balloon to atmosphere or touch contaminates.

It is another object of the invention to allow a practitioner to remove a catheter from a patient in a noncontaminated manner and to keep the catheter from any exposure to the outside environment.

It is still a further object of the invention to provide a catheter assembly in the form of a kit wherein the catheter assembly facilitates the accomplishment of the objects heretofore described.

Briefly, the invention is directed to a catheter assembly which has a catheter, a hub having the catheter slidably mounted therein and in sealing relation therewith and a collapsible sheath mounted on the hub in seal-tight relation and extending distally from the hub concentrically about the catheter. Optionally, the catheter may be of the flow directed type, and may may further include at least one lumen, and an inflatable balloon mounted at a distal end of the flow directed type catheter and being in communication with the lumen of the catheter.

In accordance with the invention, a connector is secured to a distal end of the sheath in seal-tight relation and includes a longitudinal passage for the catheter and a membrane disposed across the passage in sealed relation and in spaced relation to the distal end of the catheter in order to retain the catheter in sealed relation within the sheath and form a shielded catheter unit. The connector which is used to seal off the distal end of the catheter may be of a type as described in pending U.S. patent application Ser. No. 07/647,782, filed Jan. 30, 1991. In this respect, the connector may have a housing, for example, of transparent plastic in which a hollow metal needle is mounted to define the passage for the distal end of the catheter. In addition, the connector has a tubular portion extending from the housing which is sized to receive a male connector and a collapsible tube which is secured between the housing and the membrane within the tubular portion. In particular embodiments, the collapsible tube and the membrane may form a unitary structure. This collapsible tube serves to maintain the membrane in spaced opposed relation to the end of the hollow metal needle while sealing the catheter and may be of a configuration so that the collapsible tube is biased to return the membrane to its original spaced opposed relation when the connector is decoupled from the male connector. Further, the membrane may be constructed, for example, so to be provided with a slit, so as to permit the hollow metal needle to pierce through the membrane when the membrane is pressed into the tubular housing with the collapsible tube collapsing, as when the male connector is coupled to the connector. Preferably, the membrane and the collapsible tube are constructed of a sterilizable elastomeric material. Thereafter, the distal end of the catheter can be passed through the hollow needle.

The catheter assembly may also have a chamber assembly with an inlet port which permits for the passage of the distal end of the catheter therethrough wherein the chamber assembly is sized for receiving the balloon of a flow directed type catheter and is also sized to permit inflation of the balloon therein. In preferred embodiments, at least the portion of the chamber assembly is of a transparent material so to allow for the visual inspection of the balloon of a flow directed type catheter within the chamber assembly by visual inspection. In addition, a membrane is disposed across the inlet port of the chamber assembly in sealed relation for abutting with the membrane of the connector when the connector and the inlet port are coupled, which coupling urges the hollow metal needle of the connector through the membrane of the connector and the abutting membrane of the inlet port. Such coupling permits the subsequent passage of the tip of a flow directed type catheter through the hollow needle. In addition, a means is provided for securing the inlet port of the container assembly to the connector, which may include any effective mechanical coupling means for releasably coupling the inlet port and to the connector. Such means include but are not limited to: twist type connections such as mating threaded portions which are comprised within the connector and the inlet port which are positively coupled by twisting the mating threads into one another; mating splines or other friction fitting surface configurations wherein the connector and the inlet port include surfaces or configurations which engage one another by pushing the connector and the inlet together, and "snap-lock" type fittings wherein a first locking portion of either the container assembly or the connector are constructed to engage a mating portion of the other of either the connector or the container assembly so to form a decoupleable type fitting. Further, it is recognized that a further removable structure, such as a clip or other article may be used to retain the coupled connector and the inlet port in a coupled configuration.

In a preferred embodiment, the inlet port of the container assembly includes a pair of pins extending radially therefrom while the connector includes a pair of L-shaped slots for receiving the pins; full insertion of the inlet port of the container into the connector and rotation of one relative to one another forms a coupling which ensures the abutment of the membrane of the inlet port and the membrane of the connector, the initiation of the collapse of the collapsible tube, subsequent penetration of the hollow metal needle through both membranes, and coupling and retention of the inlet port and the connector in such position.

Where it is desired that a flow directed type catheter is to be used, and the balloon is to be preinflated, the practitioner may secure the container assembly onto the connector of the catheter assembly thereby forcing the hollow metal needle of the connector through the two membranes while maintaining a closed system. Thereafter, the distal end of the flow directed type catheter can be passed through the hollow needle and, thus, the respective sealing membranes of the connector and container assembly so to dispose the balloon within the sterile confines of the chamber portion of the container assembly. The balloon can then be inflated and inspected in the usual fashion. Thereafter, the catheter tip can then be withdrawn from the container via the hollow metal needle back within the sheath and thereafter the connector may be decoupled from container assembly. Such decoupling withdrawn the hollow metal needle from the membranes and maintains the catheter tip in a sterile condition.

The catheter assembly also has an introducer which cooperates with the sheathed catheter in order to maintain the sterility thereof. To this end, the introducer has a tubular portion of an internal cross-section sufficient to permit passage of at least the distal end of the catheter therethrough and a hub at a proximal end of the tubular portion to be releasably coupled to the connector of the catheter assembly by suitable means. In accordance with the invention, a sealing membrane is disposed across the hub of the introducer in sealed relation for abutting with the membrane of the connector when the connector and introducer are coupled with one other. This membrane may also be provided with a slit to facilitate passage of the hollow metal needle of the connector through the membrane.

In one embodiment, the introducer may also have a side port adapter assembly secured to the hub. In this case, the adaptor has a passage for the catheter therethrough with a sealing membrane being disposed across the passage for abutting with the membrane of the connector.

The construction of the catheter assembly is such that the entire distal end of the catheter including the balloon where the catheter is of the flow directed type is retained in a sterile condition within the collapsible sheath. After placement of the introducer in a blood vessel of a patient, the connector of the shielded catheter unit is coupled to the introducer, which coupling abuts the membrane of the introducer and that of the connector, and subsequently causes the hollow metal needle of the connector to pierce both said membranes and thereby provide a longitudinal passage for the catheter to pass therethrough and into the blood vessel of the patient. During this time, the membrane within the connector and the membrane of the introducer maintain sterility through the coupling operation, and ensure the continued sterility of the catheter, as it is moved into and withdrawn from the blood vessel.

In the event that a catheter requires repositioning, the catheter may be withdrawn from the introducer and via the hollow needle of the connector back within the contained sterile environment of the sheath, and the connector and the introducer decoupled. At this time, the two membranes are closed to maintain the sealed integrity of the introducer and the sheath.

These and other objects and advantages of the invention will become more apparent from the following detailed description taken in conjunction with the accompanying drawing wherein:

FIG. 1 illustrates a view of a distal end of a catheter assembly constructed in accordance with the invention;

FIG. 2 illustrates a view of a container assembly used with the catheter assembly to permit inspection of a balloon of a flow directed type catheter.

FIG. 3 illustrates a view of an introducer in a blood vessel of a patient;

FIG. 4 illustrates a cross-sectional view of a connector employed at the distal end of the catheter assembly of FIG. 1; and FIG. 5 illustrates a cross-sectional view of the connector coupled to the introducer of FIG. 3.

Referring to FIG. 1, thereon is depicted a catheter of the flow directed type. The catheter assembly 10 includes a flow directed type catheter 11 having a plurality of lumens therein, each of which communicates with a tube 12 extending from a proximal end of the catheter 11. These tubes 12 may be used for the infusion of fluids, the introduction of air, and the like. In addition, an inflatable balloon is mounted at a distal end 13 of the catheter 11 and is in communication with one of the lumens so as to receive a flow of air. It is to be understood that the catheter 11 may be of a non flow directed type and lack an inflatable balloon as is herein described; nonetheless the benefits of the instant invention will nonetheless be fully realized.

A shield 14 is also provided over the portion of the catheter 11 which includes distal end 13 thereof to form a shielded catheter unit. This shield 14 is formed by a hub 15, a connector 16 and a collapsible sheath 17. As indicated, the hub 15 is slidably mounted on the catheter 11 so as to permit the catheter 11 to slide therethrough when being implanted. The sheath 17 is mounted on the hub 15 in seal-tight relation, for example, in a manner as described in U.S. Pat. No. 4,327,723, and extends from the hub 15 concentrically about the catheter 11 including the distal portion 13 thereof. The sheath 17 may be made of any suitable material, such as a flexible transparent plastic material which permits the visual observation of the catheter 11 enclosed within.

The connector 16 is secured to the distal end of the sheath 17 in seal-tight relation as is the sheath 17 to the hub 15. This connector 16 may be constructed in a manner as described in co-pending patent application Ser. No. 07/647,782, filed Jan. 30, 1991. As shown in FIG. 4, the connector 16 has a housing 18 in which a hollow metal needle 19 is mounted to define a longitudinal passage for the catheter 11 and the distal portion 13 comprising the balloon therethrough. In addition, the connector 16 has a tubular portion 20 which is sized to receive a male connector (not shown) and a collapsible tube 21 concentric to the needle 19 and secured at one end to the housing 18, and a sealing membrane 22 disposed across the tube 21 at the proximal end of the connector 17. As may be seen from FIG. 4, the collapsible tube 21 is of a configuration which biases the shape of the tube to move the sealing membrane beyond the hollow metal needle 19 and completely envelop it when the connector 16 is in an uncoupled condition.

As illustrated, the sealing membrane 22 is disposed in spaced relation to the distal end of the hollow needle 19 in order to retain the catheter 11 in sealed relation within the sheath 16.

As indicated, the distal end 13 of the catheter 11 may be slidably disposed within the so as not to be positioned within the hollow metal needle 19 of the connector 16 in an initial position for transportation purposes.

Referring now to FIG. 2, a container assembly 23 is provided in order to permit visual inspection of the balloon located at the distal end 13 of the catheter 11 of the catheter assembly 10. The container 23 is of transparent material and has a chamber therein which communicates with an inlet port 24 through which the distal end of the catheter 11 may pass. The chamber is sized to permit inflation of the balloon located at the distal end 13 therein. In addition, a sealing membrane 25 is disposed across the end of the inlet port 24 to seal the interior chamber of the container assembly 23 as it is positioned to abut with the sealing membrane 22 of the connector 16 and to couple therewith.

A suitable means is also provided for securing the container 23 to the connector 16. As indicated, this means includes a pair of pins 26 extending from the inlet port 24 and a pair of L-shaped slots 27 (only one of which is shown) in the connector 16 for receiving the pins 26. When pre-inflation of the balloon at the distal end 13 of the catheter 11 is desired, the connector 16 of the catheter assembly 10 is connected to the inlet port 24 of the container assembly 23. At this time, the port 24 slides into the tubular portion 20 of the connector 16 while collapsing the collapsible tube 21 and abutting the two sealing membranes 22, 25 against each other in seal-tight relation. At about the same time or shortly thereafter, the hollow metal needle 19 pierces both membranes 22, 25. Thereafter, the distal end of the catheter 13 can be passed through the hollow needle 19 into the interior chamber of the container assembly 23. The balloon located at the distal end 13 can then be inflated in the usual fashion and inspected visually. Withdrawal of the catheter 11 from the container assembly 23 results in the distal end of the catheter 11 and the balloon 13 being retracted through the hollow needle 19 into the position as shown in FIG. 1. In this position, the catheter tip and balloon 13 are again in a sterile chamber. The connector 16 and the inlet port 24 are then decoupled, the hollow needle 19 is simultaneously withdrawn from the sealing membranes 22, 25 which again seals the catheter 11 at the distal end of the catheter assembly 10.

Referring to FIG. 3, the catheter assembly 10 may also employ an introducer 28 to permit implantation of the catheter 11 in a blood vessel 29. For example, the introducer 28 has a tubular portion 30 of an internal cross-section sufficient to permit passage of the catheter 11 therethrough as well as a hub 31 at a proximal end of the tubular portion 30. In the illustrated embodiment, a side port adaptor assembly 32 is also secured to the hub 31 and has a bore (not shown) for passage of the catheter 11 therethrough and a branch line 33.

The hub 31, as above, is provided with pins 26 in order to be interconnected with the connector 16 (FIG. 1) of the shielded catheter unit. In addition, the hub 31 is provided with a sealing membrane 34 disposed across the end of the hub 31 in sealed relation for abutting the membrane 22 of the connector 16 during coupling of the connector 16 and hub 31. The membrane 34 may also be provided with a slit to facilitate passage of the hollow needle 19 of the connector 16 therethrough.

In use, after the introducer 28 has been implanted in the blood vessel 29, the connector 16 of the shielded catheter unit can be connected to the hub 31 via the pins 26 and slots 27 and the catheter 11 thereafter passed through the hollow needle 19 of the connector 16 and the introducer 28 into the blood vessel 29 in a conventional fashion.

The use of the connector 16 as a part of the overall catheter assembly 10 serves to close off the distal end 13 of the catheter assembly 10 and thus maintain the catheter 11 within the sheath 17 in a sterile condition. Further, the connector 16 allows the distal end 13 which includes a balloon to be positioned within a sterile transparent container for pre-inflation and inspection. In this respect, the hollow needle 19 provides a clear passage for the distal end of the catheter 10 through the sealing membrane 22, 25. To this end, the hollow needle 19 may have a blunt end which is able to pass through the respective sealing membranes 22, 25 while maintaining a seal-tight fit therewith or in the alternative may be sharp so as to pierce through the respective sealing membranes 22, 25.

As indicated in FIG. 4, the hollow needle 19 is contained in sealed relation within the connector 16 at the distal end by means of the sealing membrane 22. As is also indicated, the distal end of the hollow needle 19 may project into a pre-formed bore within the sealing membrane 22.

As shown in FIG. 5, when the connector 16 is initially coupled to the hub 31 of the introducer 28, the hollow needle 19 provides an unobstructed longitudinal passage through the two sealing membranes 22, 34.

Thereafter, the flow directed type catheter 11 may be passed through the needle 19 into the blood vessel 29. In this respect, a given length of the catheter 11 may be threaded into the blood vessel 29 with the sheath 17 collapsing or remaining in an extended position.

The invention thus provides a catheter assembly in which all parts of the catheter which are to come in contact with a body are protected.

The present invention also provides a catheter assembly in the form of a kit which may include a container assembly or an introducer or both. Generally, the catheter assembly may be provided in the form of a kit wherein a sealed container which is suited to maintaining the sterility of its contents includes a catheter assembly as taught herein and may further include a container assembly or an introducer or both. The sealed container is preferably a transparent, partially transparent or translucent container such as a sealed at least partially rigid container as well as a flexible sealed container, such as a sealed bag or pouch.

In addition, the invention provides a catheter assembly in which the end of a catheter can be retained in a sterile condition during transportation and use. Such end may comprise a balloon if the catheter is of the flow directed type, or the catheter assembly may not comprise a balloon.

Further, the invention provides a catheter assembly which allows a practitioner to remove the catheter from a patient in a non-contaminated manner while keeping the catheter from any exposure to the outside environment.

Further, the invention provides a catheter assembly which allows a practitioner to pre-inflate or otherwise check a balloon at the tip of a flow directed type catheter for integrity as well as to flush the line under sterile conditions without exposing the balloon to atmospheric or touch contaminates.

What is claimed is:

1. A catheter assembly comprising
   a flow directed catheter;
      a hub having said catheter slidably mounted therein in sealing relation;
      a collapsible sheath mounted on said hub in seal-tight relation and extending from said hub concentrically about said catheter; and
      a connector secured to a distal end of said sheath in seal-tight relation and including
         a hollow needle defining a longitudinal passage for said catheter,
         a tubular portion about said hollow needle,
         a collapsible tube located concentrically between the tubular portion and said hollow needle, and
         a first sealing membrane disposed upon the collapsible tube and across said longitudinal passage in sealed relation and in spaced relation to said distal end of said catheter to retain said catheter in sealed relation within said sheath and moveable for movement over the hollow needle in response to collapsing of the collapsible tube.

2. A catheter assembly as set forth in claim 1 wherein the catheter is a flow directed catheter which has at least one lumen;
   and an inflatable balloon mounted at a distal end of said catheter and being in communication with said lumen.

3. A catheter assembly as set forth in claim 1 wherein said membrane has a slit for passage of said hollow needle.

4. A catheter assembly as set forth in claim 1 wherein said sheath is made of transparent plastic.

5. A catheter assembly as set forth in claim 1 for use in conjunction with a flow directed type catheter which further comprises a container assembly of transparent material having an inlet port for passage of said distal end of said catheter therethrough and a chamber portion in communication with said port for receiving said balloon of said flow directed type catheter and being sized to permit inflation of said balloon therein; and a second sealing membrane disposed across said port in sealed relation for abutting with said first membrane of said connector during passage of said hollow needle through said membranes.

6. A catheter assembly as set forth in claim 5 which further comprises means for securing said container with said connector.

7. A catheter assembly as set forth in claim 6 wherein said means includes a pair of pins extending from said port of said container and a pair of L-shaped slots in said connector for receiving said pins.

8. A catheter assembly as set forth in claim 1 which further comprises an introducer having a tubular portion of an internal cross-section sufficient to permit passage of said catheter therethrough, a hub at a proximal end of said tubular portion and a second sealing membrane disposed across said hub in sealed relation for abutting with said first membrane of said connector during passage of said hollow needle through said membranes.

9. A catheter assembly as set forth in claim 1 which further comprises an introducer having a tubular portion of an internal cross-section sufficient to permit passage of said catheter therethrough, a hub at a proximal end of said tubular portion, a side port adapter assembly secured to said hub and having a passage for said catheter and a second membrane disposed across said passage in said adapter in sealed relation for abutting with said first membrane of said connector during passage of said hollow needle through said membranes.

* * * * *